(12) United States Patent
Lanclos

(10) Patent No.: US 7,469,429 B1
(45) Date of Patent: Dec. 30, 2008

(54) EAR PROTECTION DEVICE

(76) Inventor: Ronald H. Lanclos, 1233 Canyon Way, Wellington, FL (US) 33414

( * ) Notice: Subject to any disclaimer, the term of this patent is extended or adjusted under 35 U.S.C. 154(b) by 119 days.

(21) Appl. No.: 11/340,732

(22) Filed: Jan. 27, 2006

(51) Int. Cl.
A42B 1/06 (2006.01)
(52) U.S. Cl. .......................................... 2/209
(58) Field of Classification Search .................... 2/209, 2/174, 208, 423, 455, DIG. 11; 128/864, 128/866; 132/319, 212, 213, 270
See application file for complete search history.

(56) References Cited

U.S. PATENT DOCUMENTS

| | | | |
|---|---|---|---|
| 2,729,823 A * | 1/1956 | Foster | 2/174 |
| 3,452,365 A | 7/1969 | Wallace | |
| 5,718,001 A | 2/1998 | Wright | |
| 5,920,912 A | 7/1999 | Patchett | |
| D415,861 S | 10/1999 | Marshall | |
| 6,237,157 B1 | 5/2001 | Lobbins | |
| 6,239,927 B1 * | 5/2001 | Lanzillo et al. | 259/871 |
| 6,298,493 B1 | 10/2001 | Ambroise | |
| 6,505,633 B2 * | 1/2003 | Mosely | 132/319 |
| 6,976,275 B1 * | 12/2005 | Liu | 2/423 |

* cited by examiner

Primary Examiner—Tejash Patel

(57) ABSTRACT

An ear protection device for preventing burns to an ear by a heated hair styling implement includes a pair of cuffs. Each of the cuffs is substantially J-shaped to extend around a portion of an ear. One of the cuffs is positionable along a top of the ear and the other one of the cuffs is positionable along a bottom of the ear. A telescopic arm is coupled to the cuffs to secure the cuffs together a selectable distance from each other. The groove in a first of the cuffs faces the groove in a second of the cuffs. A length of the telescopic arm is adjustable to allow a space between the cuffs to be adjusted to fit ears of different sizes.

6 Claims, 6 Drawing Sheets

EAR PROTECTION DEVICE

BACKGROUND OF THE INVENTION

1. Field of the Invention

The present invention relates to ear protectors and more particularly pertains to a new ear protector for inhibiting an ear from being burned by a heated hair styling implement.

2. Description of the Prior Art

The use of ear protectors is known in the prior art. U.S. Pat. No. 6,298,493 describes a device for extending around the periphery and an outside of an ear to protect the ear from being damaged. Another type of ear protector is U.S. Pat. No. 6,237,157 for extending around a periphery and outside of ears and being heat resistant to protect the ears from being burned by heat. Another type of ear protector is U.S. Pat. No. 5,920,912 for extending around an outside of ears to inhibit the ears from being burned.

While these devices fulfill their respective, particular objectives and requirements, the need remains for a device that has certain improved features that is adjustable to accommodate ears of various sizes and extends around the upper and lower portion of the ears to protect those portions of the ear and still allow sound to pass unimpeded to the ears.

SUMMARY OF THE INVENTION

The present invention meets the needs presented above by generally comprising a pair of cuffs. Each of the cuffs is substantially J-shaped to extend around a portion of an ear. One of the cuffs is positionable along a top of the ear and the other one of the cuffs is positionable along a bottom of the ear. A telescopic arm is coupled to the cuffs to secure the cuffs together a selectable distance from each other. The groove in a first of the cuffs faces the groove in a second of the cuffs. A length of the telescopic arm is adjustable to allow a space between the cuffs to be adjusted to fit ears of different sizes.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

The objects of the invention, along with the various features of novelty which characterize the invention, are pointed out with particularity in the claims annexed to and forming a part of this disclosure.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
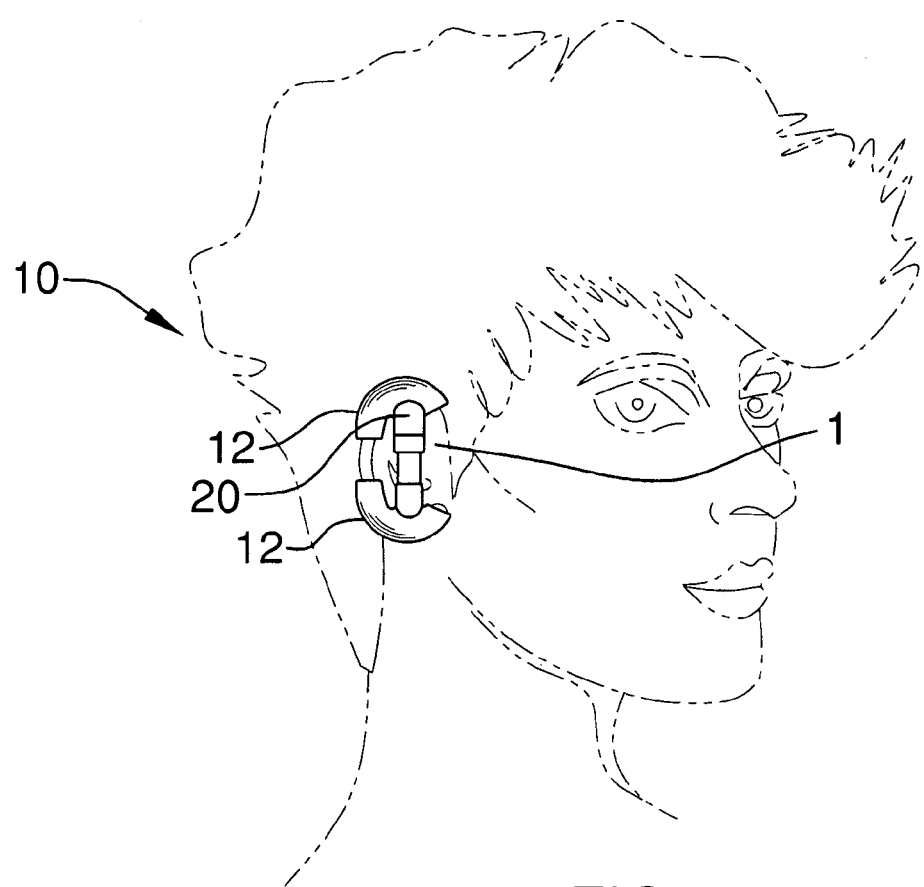
FIG. 1 is a side view of an ear protection device according to the present invention.
Figure 2:
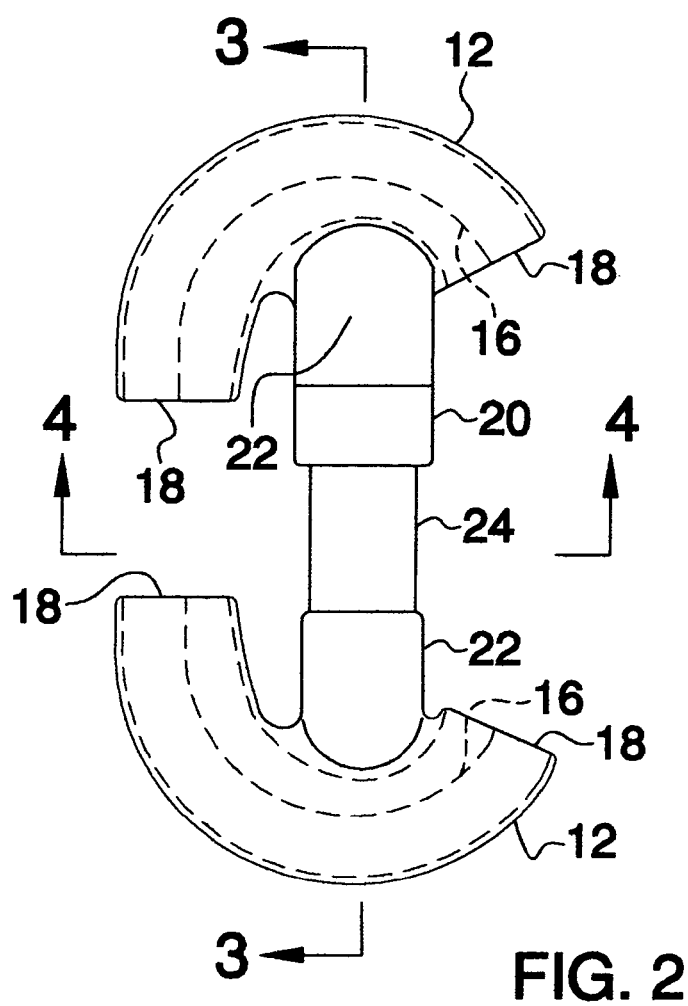
FIG. 2 is an enlarged view of the present invention.
Figure 4:
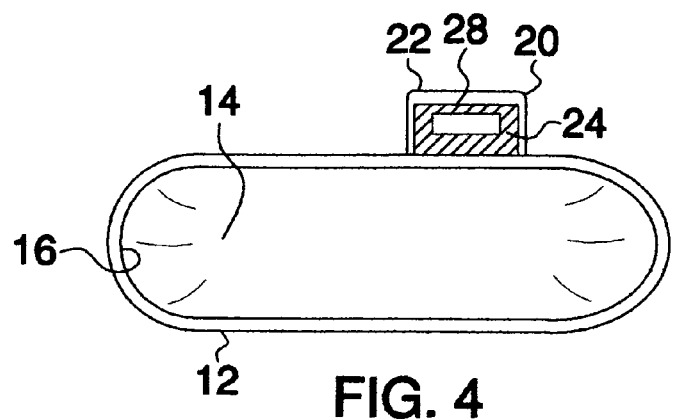
FIG. 4 is a cross-sectional view of the present invention taken along line 4-4 of FIG. 2.
Figure 3:
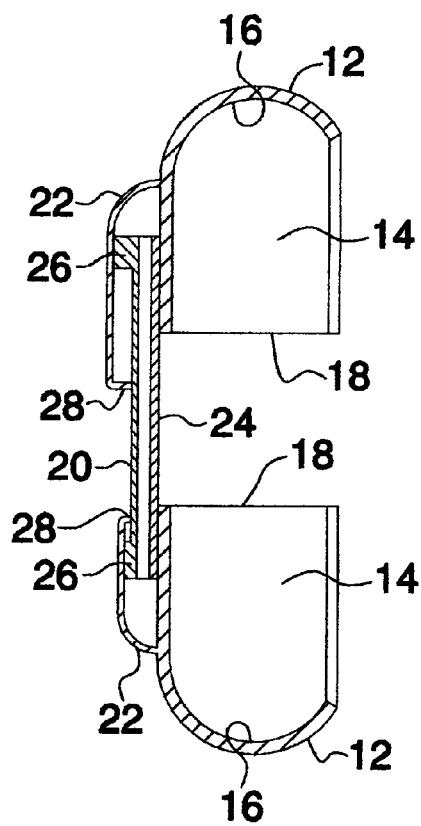
FIG. 3 is a cross-sectional view of the present invention taken along line 3-3 of FIG. 2.

With reference now to the drawings, and in particular to FIGS. 1 through 7 thereof, a new ear protector embodying the principles and concepts of the present invention and generally designated by the reference numeral 10 will be described.

As best illustrated in FIGS. 1 through 7, the ear 1 protection device 10 generally comprises a pair of oppositely directed and complimentary cuffs 12. Each of the cuffs 12 is substantially J-shaped to extend around a portion of an ear 1. One of the cuffs 12 is positionable along a top of the ear 1 and the other one of the cuffs 12 is positionable along a bottom of the ear 1. Each of the cuffs 12 has a groove 14 extending into the associated one of the cuffs 12 to form an interior face 16 to receive a portion of the ear 1 and allow the cuffs 12 to extend over a portion of the ear 1. The groove 14 extends between opposing ends 18 of the associated one of the cuffs 12.

A telescopic arm 20 is coupled to the cuffs 12 to secure the cuffs 12 together a selectable distance from each other. The groove 14 in a first of the cuffs 12 faces the groove 14 in a second of the cuffs 12. A length of the telescopic arm 20 is adjustable to allow a space between the cuffs 12 to be adjusted to fit ears 1 of different sizes.

In an embodiment, as shown in FIGS. 1 through 4, the telescopic arm 20 comprises a pair of outer portions 22. Each of the outer portions 22 is coupled to one of the cuffs 12. A base portion 24 is slidably inserted into and extends between the outer portions 22 to allow the outer portions 22 to slide along a portion of a length of the base portion 24 to adjust a distance between the cuffs 12. Each of a pair of raised tabs 26 is positioned at ends of the base portion 24 and extends outwardly from the base portion 24 and away from the cuffs 12. Each of a pair blocking tabs 28 is coupled to one of the outer portions 22 and extends inwardly towards the associated one of the cuffs 12. Each of the blocking tabs 28 slides along the base portion 24 and engages one of the raised tabs 26 to inhibit the outer portions 22 from sliding off of the base portion 24.

Figure 5:
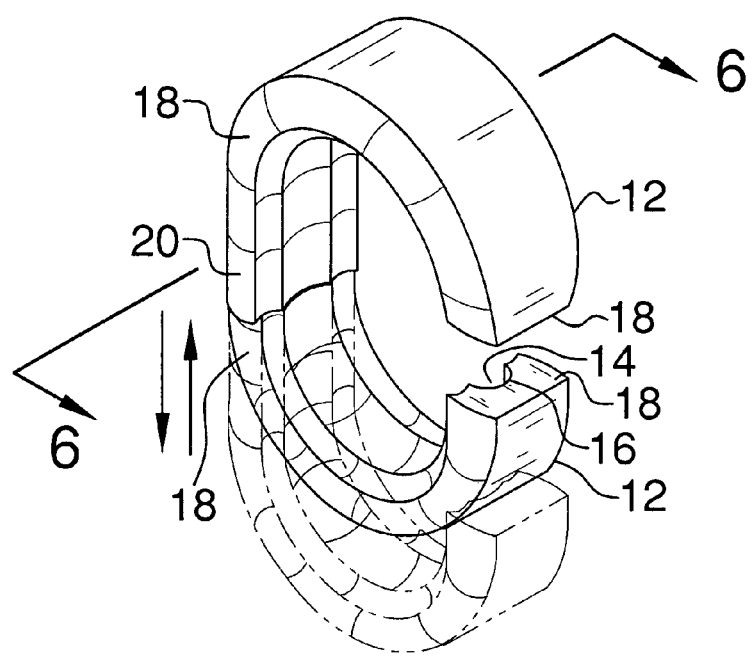
FIG. 5 is a perspective view of an embodiment of the present invention.
Figure 6:
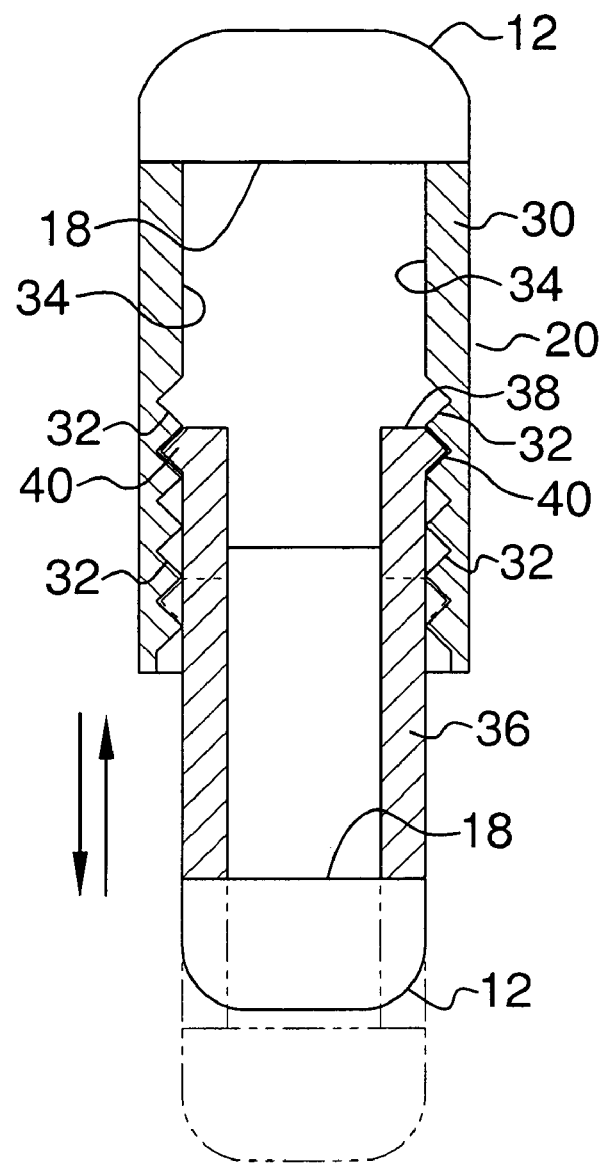
FIG. 6 is a cross-sectional view of the present invention taken along line 6-6 of FIG. 5.
Figure 7:
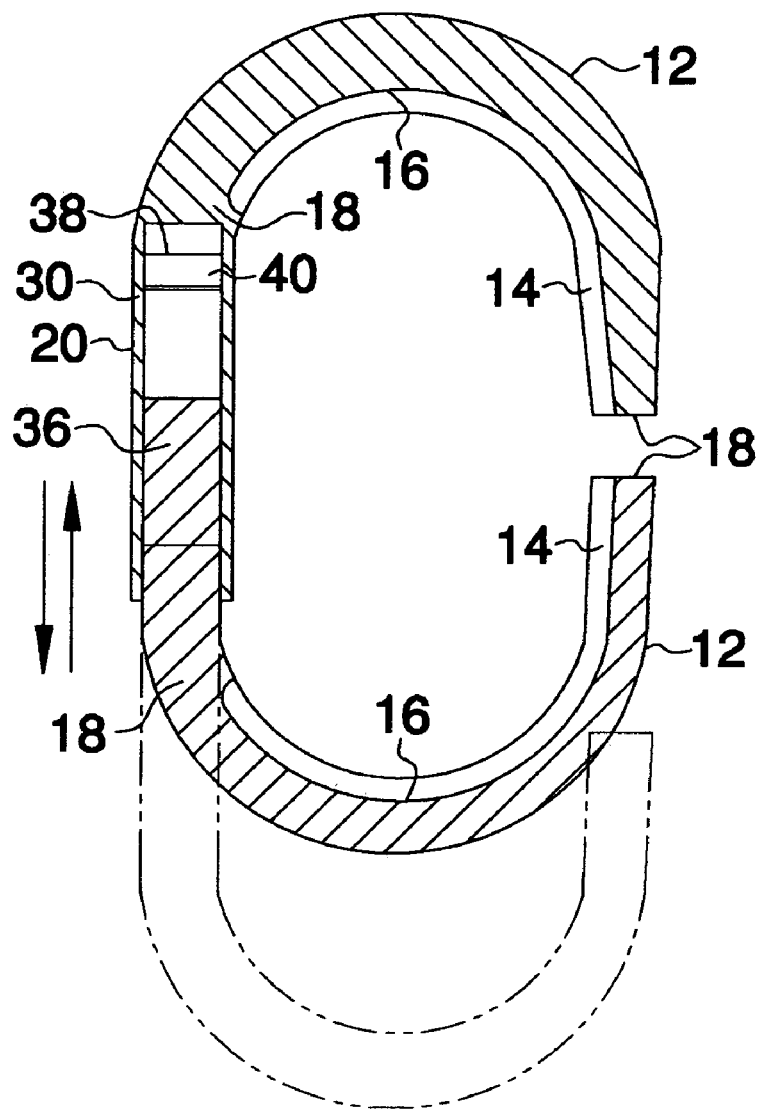
FIG. 7 is a cross-sectional view of the present invention taken along line 7-7 of FIG. 6.

In an embodiment, as shown in FIGS. 5 through 7, the telescopic arm 20 includes an upper portion 30 coupled to one of the cuffs 12. The upper portion 30 has a plurality of notches 32 being aligned along opposing interior side faces 34 of the upper portion 30. A lower portion 36 is coupled to the other one of the cuffs 12. A free end 38 of the lower portion 36 is slidably inserted into the upper portion 30. The lower portion 36 slides along the interior side faces 34 to allow a length of the telescopic arm 20 to be adjusted. Each of a pair of nubs 40 is coupled to the lower portion 36 adjacent to the free end 38 of the lower portion 36. Each of the nubs 40 extends outwardly from the lower portion 36 and engages one of the notches 32 of the upper portion 30 to releasably secure the lower portion 36 at a desired location.

In use, the length of the telescopic arm 20 is adjusted to accommodate the ear 1. The top of the ear 1 is inserted into the groove 14 of one of the cuffs 12 and the bottom of the ear 1 is inserted into the groove 14 of the other one of the cuffs 12. The cuffs 12 inhibit the ear 1 from being burned when the ear 1 is in close proximity to a heated hair styling implement.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. An ear protection device comprising:
   a pair of cuffs, each of said cuffs being substantially J-shaped to extend around a portion of an ear, one of said cuffs being positionable along a top of the ear and the other one of said cuffs being positionable along a bottom of the ear, each of said cuffs having a groove extending into the associated one of said cuffs to form an interior face to receive a portion of the ear and allow said cuffs to extend over a portion of the ear, said groove in said cuff positioned along the top of the ear being directed downward and said groove in said cuff positioned along a bottom of the ear being directed upwardly; and
   a telescopic arm being coupled to said cuffs to secure said cuffs together a selectable distance from each other, said groove in a first of said cuffs facing said groove in a second of said cuffs, a length of said telescopic arm being adjustable to allow a space between said cuffs to be adjusted to fit ears of different sizes.

2. The device according to claim 1, wherein said groove extends between opposing ends of the associated one of said cuffs.

3. The device according to claim 1, wherein said telescopic arm comprises a pair of outer portions, each of said outer portions being coupled to one of said cuffs, a base portion being slidably inserted into and extending between said outer portions to allow said outer portions to slide along a portion of a length of said base portion to adjust a distance between said cuffs.

4. The device according to claim 3, wherein a pair of raised tabs positioned at ends of said base portion and extending outwardly from said base portion and away from said cuffs, a pair of blocking tabs, each of said blocking tabs being coupled to one of said outer portions and extending inwardly towards the associated one of said cuffs, each of said blocking tabs sliding along said base portion and engaging one of said raised tabs to inhibit said outer portions from sliding off of said base portion.

5. The device according to claim 1, wherein said telescopic arm comprises an upper portion coupled to one of said cuffs, a lower portion being coupled to the other one of said cuffs, a free end of said lower portion being slidably inserted into said upper portion, said lower portion sliding along a portion of a length of said upper portion to allow a length of said telescopic arm to be adjusted.

6. The device according to claim 5, wherein said upper portion has a plurality of notches being aligned along opposing interior side faces of said upper portion, a pair of nubs, each of said nubs being coupled to said lower portion adjacent to said free end of said lower portion, each of said nubs extending outwardly from said lower portion and engaging one of said notches of said upper portion to releasably secure said lower portion at a desired location.

* * * * *